(12) United States Patent
Hassinen et al.

(10) Patent No.: US 12,389,901 B2
(45) Date of Patent: Aug. 19, 2025

(54) TEMPERATURE-RESPONSIVE VIRUS STORAGE SYSTEM

(71) Applicant: Trizell Ltd., West Drayton (GB)

(72) Inventors: Minna Hassinen, Kuopio (FI); Nigel Parker, Chinnor (GB); Robert Shaw, Kuopio (FI)

(73) Assignee: FERRING VENTURES LTD, West Drayton (GB)

( * ) Notice: Subject to any disclaimer, the term of this patent is extended or adjusted under 35 U.S.C. 154(b) by 0 days.

(21) Appl. No.: 18/906,588

(22) Filed: Oct. 4, 2024

(65) Prior Publication Data

US 2025/0024830 A1 Jan. 23, 2025

Related U.S. Application Data

(63) Continuation-in-part of application No. 18/538,052, filed on Dec. 13, 2023, which is a continuation-in-part of application No. 17/912,103, filed as application No. PCT/IB2021/000157 on Mar. 19, 2021.

(60) Provisional application No. 62/991,671, filed on Mar. 19, 2020.

(51) Int. Cl.
*A01N 1/125* (2025.01)
*C12N 1/04* (2006.01)

(52) U.S. Cl.
CPC ................................... *A01N 1/125* (2025.01)

(58) Field of Classification Search
None
See application file for complete search history.

(56) References Cited

U.S. PATENT DOCUMENTS

2005/0085427 A1 4/2005 Connor et al.
2009/0098632 A1 4/2009 Frei et al.

OTHER PUBLICATIONS

Diana K. Hoganson, et al. Development of a Stable Adenoviral Vector Formulation. BioProcessing Journal. 1. 43-48. 10.12665/J11. Sosnowski. Bioprocessing Journal, I(1):43-48 (Mar. 2002).
L. van den Berg et al., "Effect of freezing on the pH and composition of sodium and potassium phosphate solutions: the reciprocal system $KH_2PO_4$-$Na_2HPO_4$-$H_2O$" Archives of Biochemistry and Biophysics, vol. 81, Issue 2, Apr. 1959, pp. 319-329.

*Primary Examiner* — Michail A Belyavskyi
(74) *Attorney, Agent, or Firm* — Lisa Mueller; Casimir Jones SC

(57) ABSTRACT

A temperature-responsive virus storage system that allows virus to be stored, such as a non-frozen liquid, and maintain infectivity is described.

5 Claims, No Drawings

TEMPERATURE-RESPONSIVE VIRUS STORAGE SYSTEM

RELATED APPLICATION INFORMATION

This application is a continuation-in-part of U.S. application Ser. No. 18/538,052, which is a continuation-in-part of U.S. application Ser. No. 17/912,103 filed on Sep. 16, 2022, which is a § 371 National Phase Entry of PCT/IB202/000157, filed on Mar. 19, 2021, which claims the benefit of U.S. Provisional Patent Application No. 62/991,671 filed Mar. 19, 2020, the entire contents of each of which are hereby incorporated by reference.

BACKGROUND

Infectious viruses are useful as e.g., vaccines and gene therapy vectors. Viruses, however, lose infectivity over time.

One method that the art teaches to preserve virus infectivity is by freezing. The art teaches to either store infectious virus suspended in a frozen storage buffer, or to freeze the virus suspension and then remove the frozen storage buffer by freeze-drying to produce a dried lyophilized product.

Regardless of whether freezing entails subsequent drying/lyophilization, however, freezing can damage viruses, reducing infectivity. One traditional way that the art addresses this is by adding cryo-protectants. For example, the art teaches to freeze infective virus in suspension in saline containing 10 to 30% of glycerol as a cryo-protectant (Graham et al., 1991, *Methods in Molecular Biology*, vol. 7, chapter 11, p. 109-127; Ed Murrey The Human Press Inc.; Precious and Russel, *Virology, a Practical Approach*, 1985, chapter 9, p. 193-205; ed: B W Mahy, IRL Press, Washington DC; Kanegae et al., Jpn. J. Med. Sci. Biol., 47, 157-166, 1994 and Green et al., *Methods in Enzymology*, vol. LVIII, p. 425-435), PCT patent publication WO98/02522. Glycerol reduces the damage that viruses incur during the freeze-thaw process, preserving infectivity somewhat. However, the art teaches that glycerol has the disadvantage of irritating the pulmonary epithelium, which may be unacceptable in the case of intra-tracheal and intra-pulmonary administration (for example for the treatment of cystic fibrosis or of cancers of the pulmonary tract).

Sucrose at a low concentration (1 to 5%) to a saline has also been used as a cryo-protectant for frozen virus suspensions (Precious et al., see above; Huyghe et al., *Human Gene Therapy* 6:1403-1416 November 1995, and Rehir, *Process Development and Production Issues for Viral Vectors & Vaccines*, The Williamsburg Bio Processing Conference, 2nd annual meeting, Nov. 6-9, 1995).

The use of lactose or sucrose at low concentrations (2.5-5%) for the cryo-preservation of live viruses has also been recommended (see JP88/555465).

Cryo-protectants reduce freezing damage. They do not, however, eliminate it. The art thus needs a way to preserve virus in a non-frozen form, where the virus retains a significant amount of its original infectivity.

SUMMARY

In one aspect, the present disclosure features a composition comprising infectious viral particles, tromethamine and cyclodextrin, wherein the composition comprises about $1 \times 10^6$ to about $1 \times 10^{12}$, about $1 \times 10^7$ to about $1 \times 10^{12}$, about $1 \times 10^8$ to about $1 \times 10^{12}$, about $1 \times 10^9$ to about $1 \times 10^{12}$ cyclodextrin molecules per viral particle (e.g., about $1 \times 10^6$, about $1 \times 10^7$, about $1 \times 10^8$, about $1 \times 10^9$, about $1 \times 10^{10}$, about $1 \times 10^{11}$, or about $1 \times 10^{12}$ cyclodextrin molecules per viral particle). In another aspect, the composition comprising infectious viral particles, cyclodextrin, tromethamine, and sodium phosphate, wherein the composition comprises about 1 to about 1.5 moles of tromethamine per mole of sodium phosphate (e.g., about 1, 1.1, 1.2, 1.3, 1.4, or 1.5 moles of tromethamine per mole of sodium phosphate).

In some embodiments, the composition comprises a cryoprotectant (e.g., a cryoprotective-effective amount of glycerol, sucrose, or both).

In some embodiments, the composition comprises glycerol in a relative amount of about 50 times, about 60 times, about 70 times, about 80 times, about 90 times, about 100 times, about 200 times, about 300 times, about 400 times, about 500 times, about 600 times, or about 700 times the amount of tromethamine (w/w). In some embodiments, the composition comprises sucrose in a relative amount of about 10 times, about 11 times, about 12 times, about 13 times, about 14 times, about 15 times, about 16 times, about 17 times, about 18 times, about 19 times, about 20 times, about 30 times, about 40 times, about 50 times, about 60 times, about 70 times, about 80 times, about 90 times, about 100 times, about 110 times, about 120 times, or about 130 times the amount of tromethamine (w/w).

In some embodiments, the cyclodextrin is hydroxypropyl beta-cyclodextrin. In some embodiments, hydroxypropyl beta-cyclodextrin in a relative amount of about 5 times, about 6 times, or about 7 times the amount of tromethamine (w/w).

In some embodiments, the composition further comprises (3α, 5β, 7α, 12α)-N-[3-[(4-O-D-galactopyranosyl-D-gluconoyl)amino]propyl]-3,7,12-trihydroxy-N-[3-[[(3α, 5β, 7α, 12α]-3,7,12-trihydroxy-24-oxocholan-24-yl]amino]propyl]-cholan-24-amide (NODA). In some embodiments, the composition comprises NODA in a relative amount of about 0.5 times, about 0.6 times, about 0.7 times, about 0.8 times, about 0.9 times, or about 1 times the amount of tromethamine (w/w).

In some embodiments, the sodium phosphate is sodium dihydrogen phosphate dehydrate. In some embodiments, the composition further comprises magnesium chloride, polysorbate 80, sodium citrate, and citric acid.

In some embodiments, the virus is present in an amount of about $1 \times 10^{11}$ viral particles per milliliter of composition.

In some embodiments, the composition has a first pH at a first temperature, and a second pH at a second temperature, wherein the first temperature is lower than the second temperature, and the first pH is higher than the second pH. In some embodiments, the first temperature is about −60° C., about −20° C., about −0° C., about 4° C., and the first pH is a basic pH. In some embodiments, the second temperature is about 20° C. to about 25° C., and the second pH is an acidic pH.

In some embodiments, the composition is stored frozen (e.g., such as in a freezer), as a frozen suspension, at a temperature less than or equal to about −60° C. In some embodiments, the composition is stored frozen at temperature of about −60° C. to about −100° C. In other embodiments, the composition is stored frozen at temperature of about −60° C. to about −90° C. In still yet other embodiments, composition is stored frozen at temperature of about −60° C. to about −80° C. In some embodiments, the composition is stored frozen at a temperature of about −60° C. In some embodiments, the composition is stored frozen at a temperature of less than or equal to about −60° C., about −60° C. to about −100° C., about −60° C. to about −90° C., or about −60° C. to about −80° C., for a period of time of about 3 months, 6 months, 9 months, 12 months, 15 months, 18 months, 21 months, 24 months, 36 months, 48 months, or longer. In some embodiments, the composition is stored frozen at a temperature of about −60° C., for a period of time of about 3 months, 6 months, 9 months, 12 months, 15 months, 18 months, 21 months, 24 months, 36 months, 48 months, or longer.

In still yet further embodiments, the composition is stored frozen (e.g., in a freezer), as a frozen suspension for a period of up to 3 months at a temperature between about −35° C. to about −10° C. In still yet other embodiments, the composition is stored frozen for a period of up to 3 months at a temperature between about −25° C. to about −15° C.

The frozen composition must be thawed and brought to room temperature (e.g., about 20° C. to about 25° C.) prior to administration to a subject. Once thawed, the composition can be stored as a liquid (e.g., a suspension), in a non-frozen state: (a) for up to 24 hours at room temperature; (b) at about 2° C. to about 8° C. (e.g., in a refrigerator) for up to 1 day, up to 2 days, up to 3 days, up to 4 days, up to 5 days, up to 6 days, or up to 7 days; (c) at about 2° C. to about 8° C. for up to 1 day, up to 2 days, up to 3 days, up to 4 days, up to 5 days, up to 6 days, or up to 7 days followed by up to 24 hours at room temperature; or (d) in a syringe for up to 1 hour, up to two hours, up to three hours, up to four hours, up to five hours or up to six hours.

In some embodiments, after storage as in a frozen state, at a temperature of about −60° C. to about −100° C., about −60° C. to about −90° C., or about −60° C. to about −80° C., for about 3 months, 6 months, 9 months, 12 months, 15 months, 18 months, 21 months, 24 months, 36 months, 48 months, or longer, the viral particles retain at least about 70%, 80%, 90%, or 95% of the initial total viral particle concentration, and/or retain at least about 60%, 70%, 80%, 90%, or 95% of their initial infectious titer. In some embodiments, infectious titer is measured as Normalized and Adjusted Standard-Infectious Units (NAS IU).

In still yet further embodiments, after storage in a frozen state at a temperature of about −35° C. to about −10° C., or about −25° C. to about −15° C., for about 3 months, the viral particles retain at least about 70%, 80%, 90%, or 95% of the initial total viral particle concentration, and/or retain at least about 60%, 70%, 80%, 90%, or 95% of their initial infectious titer. In some embodiments, infectious titer is measured as Normalized and Adjusted Standard—Infectious Units (NAS IU).

In some embodiments, the infectious virus is a lentivirus, adenovirus or adeno-associated virus. In some embodiments, the infectious virus is a replication-deficient adenovirus.

In another aspect, the disclosure features a composition comprising sodium dihydrogen phosphate dehydrate, tromethamine, glycerol, sucrose, hydroxypropyl beta-cyclodextrin, NODA, and infectious replication-deficient adenovirus, wherein the composition comprises: tromethamine in a relative amount of about 1.3 moles of tromethamine per mole of sodium dihydrogen phosphate dehydrate; glycerol in a relative amount of about 60 times the amount of tromethamine (w/w); sucrose in a relative amount of about 12 times the amount of tromethamine (w/w); hydroxypropyl beta-cyclodextrin in a relative amount of about 6 times the amount of tromethamine (w/w); NODA in a relative amount of about 0.7 times the amount of tromethamine (w/w); and about $1\times10^{11}$ replication-deficient adenovirus particles per milliliter of composition. In some embodiments, the composition comprises a first formulation comprising sodium dihydrogen phosphate dehydrate, tromethamine, glycerol, sucrose, hydroxypropyl beta-cyclodextrin, NODA, and infectious replication-deficient adenovirus, wherein the composition comprises: tromethamine in a relative amount about 1.3 moles of tromethamine per mole of sodium dihydrogen phosphate dehydrate; glycerol in a relative amount of about 60 times the amount of tromethamine (w/w); sucrose in a relative amount of about 12 times the amount of tromethamine (w/w); hydroxypropyl beta-cyclodextrin in a relative amount of about 6 times the amount of tromethamine (w/w); NODA in a relative amount of about 0.7 times the amount of tromethamine (w/w); wherein the composition comprises about 1 part of the first formulation and about 10 parts water, and about $1\times10^{11}$ or about $3\times10^{11}$ replication-deficient adenovirus particles per milliliter of composition. In yet another aspect, the disclosure features a composition comprising sodium dihydrogen phosphate dehydrate, tromethamine, glycerol, sucrose, hydroxypropyl beta-cyclodextrin, NODA, and infectious replication-deficient adenovirus, wherein the composition comprises: tromethamine in a relative amount of from about 1 to about 1.5 moles of tromethamine per mole of sodium dihydrogen phosphate dehydrate; glycerol in a relative amount of about 600 times the amount of tromethamine (w/w); sucrose in a relative amount of about 120 times the amount of tromethamine (w/w); hydroxypropyl beta-cyclodextrin in a relative amount of about 6 times the amount of tromethamine (w/w); NODA in a relative amount of about 0.7 times the amount of tromethamine (w/w); and about $1\times10^{11}$ replication-deficient adenovirus particles per milliliter of composition. In some embodiments, the composition comprises a first formulation comprising sodium dihydrogen phosphate dehydrate, tromethamine, glycerol, sucrose, hydroxypropyl beta-cyclodextrin, NODA, and infectious replication-deficient adenovirus, wherein the composition comprises: tromethamine in a relative amount of from about 1 to about 1.5 moles of tromethamine per mole of sodium dihydrogen phosphate dehydrate; glycerol in a relative amount of about 600 times the amount of tromethamine (w/w); sucrose in a relative amount of about 120 times the amount of tromethamine (w/w); hydroxypropyl beta-cyclodextrin in a relative amount of about 6 times the amount of tromethamine (w/w); NODA in a relative amount of about 0.7 times the amount of tromethamine (w/w); wherein the composition comprises about 1 part of the first formulation and about 10 parts water, and about $1\times10^{11}$ or about $3\times10^{11}$ replication-deficient adenovirus particles per milliliter of composition.

In another aspect, the disclosure features a composition comprising infectious viral particles, tromethamine and cyclodextrin, the cyclodextrin present in a relative amount of from about $1\times10^{6}$ to about $1\times10^{12}$ cyclodextrin molecules per viral particle, the tromethamine able to change pH in response to change in temperature, the tromethamine present in an amount whereby if the composition is stored in a liquid, non-frozen state, or at a frozen state, at −20° C. for one year, the viral particles retain at least about 95% of the initial total viral particle concentration and at least about 80% of their initial infectious titer measured as NAS IU. In still other embodiments, the disclosure features a composition comprising infectious viral particles, tromethamine and cyclodextrin, the cyclodextrin present in a relative amount of from about $1\times10^{6}$ to about $1\times10^{12}$ cyclodextrin molecules per viral particle, the tromethamine able to change pH in response to change in temperature, the tromethamine present in an amount whereby if the composition is stored in a liquid, non-frozen state, or at a frozen state, at −20° C. for one year, the viral particles retain at least about 95% of the initial total viral particle concentration and at least about 80% of their initial infectious titer measured as NAS IU.

In another aspect, the disclosure features a composition comprising infectious viral particles, tromethamine and cyclodextrin, the cyclodextrin present in a relative amount of from about $1 \times 10^6$ to about $1 \times 10^{12}$ cyclodextrin molecules per viral particle, the tromethamine able to change pH in response to change in temperature, the tromethamine present in an amount whereby if the composition is stored in a frozen state, at less than or equal to about −60° C. (such as for example, less than or equal to about −60° C. to about −100° C., about −60° C. to about −90° C., or about −60° C. to about −80° C., or about −60° C.) for at least one year, the viral particles retain at least about 95% of the initial total viral particle concentration and at least about 80% of their initial infectious titer measured as NAS IU. In still other embodiments, the disclosure features a composition comprising infectious viral particles, tromethamine and cyclodextrin, the cyclodextrin present in a relative amount of from about $1 \times 10^6$ to about $1 \times 10^{12}$ cyclodextrin molecules per viral particle, the tromethamine able to change pH in response to change in temperature, the tromethamine present in an amount whereby if the composition is stored in a frozen state, at less than or equal to about −60° C. (such as for example, less than or equal to about −60° C. to about −100° C., about −60° C. to about −90° C., or about −60° C. to about −80° C., or about −60° C.) for one year, the viral particles retain at least about 95% of the initial total viral particle concentration and at least about 80% of their initial infectious titer measured as NAS IU.

In some embodiments, the composition further comprises sodium phosphate present in a relative amount of from about 1 to about 1.5 moles of tromethamine per mole of sodium phosphate. In some embodiments, the sodium phosphate is sodium dihydrogen phosphate dehydrate. In other embodiments, the composition further comprises sodium phosphate present in a relative amount of from about 1 to about 1.3 moles of tromethamine per mole of sodium phosphate. In some embodiments, the sodium phosphate is sodium dihydrogen phosphate dehydrate.

In some embodiments, the composition further comprises a cryoprotective-effective amount of glycerol, sucrose, or both. In some embodiments, the composition comprises glycerol in a relative amount of about 60 times the amount of tromethamine (w/w), and the composition comprises sucrose in a relative amount of about 12 times the amount of tromethamine (w/w). In still other embodiments, the composition further comprises a cryoprotective-effective amount of glycerol, sucrose, or both. In some embodiments, the composition comprises glycerol in a relative amount of about 600 times the amount of tromethamine (w/w), and the composition comprises sucrose in a relative amount of about 120 times the amount of tromethamine (w/w).

In some embodiments, the cyclodextrin is hydroxypropyl beta-cyclodextrin. In some embodiments, the composition comprises hydroxypropyl beta-cyclodextrin in a relative amount of about 6 times the amount of tromethamine (w/w).

In some embodiments, the infectious virus is a lentivirus, adenovirus or adeno-associated virus. In some embodiments, the infectious virus is a replication-deficient adenovirus.

In some embodiments, the composition further comprises NODA in a relative amount of about 0.7 times the amount of tromethamine (w/w), and wherein the virus is present in an amount of about $1 \times 10^{11}$ viral particles per milliliter of composition.

In some embodiments, the composition further comprises sodium dihydrogen phosphate dehydrate present in a relative amount of from about 1 to about 1.5 moles of tromethamine per mole of sodium dihydrogen phosphate dehydrate, and further comprising glycerol and sucrose, the glycerol present in a relative amount of about 60 times the amount of tromethamine (w/w) and the sucrose present in a relative amount of about 12 times the amount of tromethamine (w/w), wherein the cyclodextrin comprises hydroxypropyl beta-cyclodextrin in a relative amount of about 6 times the amount of tromethamine (w/w), wherein the infectious virus comprises replication-deficient adenovirus, and further comprising NODA in a relative amount of about one times the amount of tromethamine (w/w), where the virus is present in an amount of about $1 \times 10^{11}$ viral particles per milliliter of composition. In still yet other embodiments, the composition further comprises sodium dihydrogen phosphate dehydrate present in a relative amount of from about 1 to about 1.5 moles of tromethamine per mole of sodium dihydrogen phosphate dehydrate, and further comprising glycerol and sucrose, the glycerol present in a relative amount of about 600 times the amount of tromethamine (w/w) and the sucrose present in a relative amount of about 120 times the amount of tromethamine (w/w), wherein the cyclodextrin comprises hydroxypropyl beta-cyclodextrin in a relative amount of about 6 times the amount of tromethamine (w/w), wherein the infectious virus comprises replication-deficient adenovirus, and further comprising NODA in a relative amount of about one times the amount of tromethamine (w/w), where the virus is present in an amount of about $1 \times 10^{11}$ viral particles per milliliter of composition.

In another aspect, the disclosure features a method of preserving level of infectivity of an infective virus. In some embodiments, the method comprises storing the composition of any of the aspects described herein in a liquid, non-frozen state, or in a frozen state, at about −60° C. or at about −20° C., for about 3 months, 6 months, 9 months, 12 months, 15 months, 18 months, 21 months, 24 months or longer. In some embodiments, the viral particles retain at least about 70%, 80%, 90%, or 95% of the initial total viral particle concentration, and/or retain at least about 60%, 70%, 80%, 90%, or 95% of their initial infectious titer. In some embodiments, infectious titer is measured as Normalized and Adjusted Standard-Infectious Units (NAS IU).

In another aspect, the disclosure features a method of preserving level of infectivity of an infective virus. In some embodiments, the method comprises storing the composition of any of the aspects described herein in a frozen state, at a temperature of about −60° C. to about −100° C., about −60° C. to about −90° C., or about −60° C. to about −80° C., for about 3 months, 6 months, 9 months, 12 months, 15 months, 18 months, 21 months, 24 months, 36 months, 48 months, or longer. In some embodiments, the viral particles retain at least about 70%, 80%, 90%, or 95% of the initial total viral particle concentration, and/or retain at least about 60%, 70%, 80%, 90%, or 95% of their initial infectious titer. In some embodiments, infectious titer is measured as Normalized and Adjusted Standard-Infectious Units (NAS IU). In still yet other embodiments, the method comprises storing the composition of any of the aspects described herein in a frozen state at a temperature of about −35° C. to about −10° C., or about −25° C. to about −15° C. for about 3 months. In some embodiments, the viral particles retain at least about 70%, 80%, 90%, or 95% of the initial total viral particle concentration, and/or retain at least about 60%, 70%, 80%, 90%, or 95% of their initial infectious titer. In some embodiments, infectious titer is measured as Normalized and Adjusted Standard-Infectious Units (NAS IU).

In another aspect, the disclosure features a method of treating a subject suffering from cancer. In some embodiments, the method comprises administering to the subject the composition of any one of the aspects described herein. In some embodiments, wherein the viral particles are recombinant adenoviral particles encoding human interferon α-2b.

Definitions

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

A or An: The articles "a" and "an" are used herein to refer to one or to more than one (i.e., to at least one) of the grammatical object of the article. By way of example, "an element" means one element or more than one element.

Administration: As used herein, the term "administration" typically refers to the administration of a composition to a subject or system. Those of ordinary skill in the art will be aware of a variety of routes that may, in appropriate circumstances, be utilized for administration to a subject, for example a human. For example, in some embodiments, administration may be ocular, oral, parenteral, or topical. Examples of parental routes include, without limitation, intravesical, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal, intracoronary, intracorporus, intracranial, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intraocular, intrasinal, intraspinal, intrasynovial, intratendinous, intratesticular, intrathecal, intrathoracic, intratubular, intratympanic, intrauterine, intravascular, intravenous (e.g., bolus or drip), intraventricular, and subcutaneous. In some embodiments, administration comprises intravesical administration. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Approximately or About: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Cancer: The terms "cancer," "malignancy," "neoplasm," "tumor," and "carcinoma," are used herein to refer to cells that exhibit relatively abnormal, uncontrolled, and/or autonomous growth, so that they exhibit an aberrant growth phenotype characterized by a significant loss of control of cell proliferation. In some embodiments, a tumor may be or comprise cells that are precancerous (e.g., benign), malignant, pre-metastatic, metastatic, and/or non-metastatic. The present disclosure specifically identifies certain cancers to which its teachings may be particularly relevant. In some embodiments, a cancer may be characterized by a solid tumor. In some embodiments, a cancer may be characterized by a hematologic tumor. In general, examples of different types of cancers known in the art include, for example, hematopoietic cancers including leukemias, lymphomas (Hodgkin's and non-Hodgkin's), myelomas and myeloproliferative disorders; sarcomas, melanomas, adenomas, and carcinomas of solid tissue; squamous cell carcinomas of the mouth, throat, larynx, and lung; liver cancer; genitourinary cancers, such as prostate, cervical, bladder, uterine, endometrial cancer, or renal cell carcinomas; bone cancer; pancreatic cancer; skin cancer; cutaneous or intraocular melanoma; cancer of the endocrine system; cancer of the thyroid gland; cancer of the parathyroid gland; head and neck cancers; breast cancer; gastro-intestinal cancers; nervous system cancers; and benign lesions, such as papillomas. In some embodiments, a cancer comprises or is a bladder cancer, e.g., a high-grade non-muscle-invasive bladder cancer (NMIBC). In some embodiments, a cancer comprises or is carcinoma in situ (CIS) and/or high-grade papillary disease. In some embodiments, a cancer comprises or is Ta or T1 bladder cancer. In some embodiments, a cancer comprises or is a *Bacillus* Calmette-Guerin (BCG)-resistant cancer.

Pharmaceutical composition: As used herein, the term "pharmaceutical composition" refers to a composition in which an active agent is formulated together with one or more pharmaceutically acceptable carriers. In some embodiments, the active agent is present in unit dose amount appropriate for administration in a therapeutic regimen that shows a statistically significant probability of achieving a predetermined therapeutic effect when administered to a relevant population. A pharmaceutical composition may be specially formulated for administration in solid or liquid form, including those adapted for the following: oral administration, for example, drenches (aqueous or non-aqueous solutions or suspensions), tablets (e.g., targeted for buccal, sublingual, and systemic absorption), boluses, powders, granules, pastes for application to the tongue; parenteral administration, for example, by intravesical, subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces. In certain embodiments, a pharmaceutical composition is formulated as a suspension (e.g., sterile suspension) for intravesical instillation. In some embodiments, a pharmaceutical composition is intended and suitable for administration to a human subject.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Subject: As used herein, the term "subject" refers to an organism, for example, a mammal (e.g., a human, a non-human mammal, a non-human primate, a primate, a laboratory animal, a mouse, a rat, a hamster, a gerbil, a cat, or a dog). In some embodiments, a human subject is an adult, adolescent, or pediatric subject. In some embodiments, a subject is suffering from a disease, disorder or condition, e.g., a disease, disorder or condition that can be treated as provided herein, e.g., a cancer or a tumor listed herein (e.g., a bladder cancer or tumor, e.g. high-grade non-muscle-invasive bladder cancer (NMIBC)). In some embodiments, a subject is susceptible to a disease, disorder, or condition. In some embodiments, a susceptible subject is predisposed to and/or shows an increased risk (as compared to the average risk observed in a reference subject or population) of developing the disease, disorder, or condition. In some embodiments, a subject has been diagnosed with one or more diseases, disorders or conditions. In some embodiments, a subject displays one or more symptoms of a disease, disorder or condition. In some embodiments, a subject does not display a particular symptom (e.g., clinical manifestation of disease) or characteristic of a disease, disorder, or condition. In some embodiments, a subject does not display any symptom or characteristic of a disease, disorder, or condition. In some embodiments, a subject is a patient. In some embodiments, a subject is an individual to whom diagnosis and/or therapy is and/or has been administered. In some embodiments, a subject is receiving or has received certain therapy to diagnose and/or to treat a disease, disorder, or condition.

Treatment: As used herein, the term "treatment" (also "treat" or "treating") refers to any administration of a therapy that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

DETAILED DESCRIPTION

The present disclosure is based, in part, on the discovery of a way to preserve virus infectivity without freezing and/or without storing in a frozen state. The discovery uses cyclodextrin (a cyclic oligosaccharide) as an agent to protect the virus, and a liquid storage buffer that can change pH, e.g., in response to changes in temperature. Without intending to be bound by theory, it is believed that at a more basic pH, the buffer affects the charge within the interior cavity of a cyclodextrin, promoting viral capsid polypeptides to bind to the interior. While associated with the cyclodextrin interior, the virus is physically sheltered from the damaging effects of low temperature. At more acidic pH, the buffer has the opposite effect, such that viral capsid polypeptides are no longer bound to the interior cavity of a cyclodextrin, promoting release of the virus from the cyclodextrin. This system thus enables a pH-dependent switch, such that virus can be loaded into the cyclodextrin interior for protection during storage, and then the virus can be subsequently released from the cyclodextrin.

In some embodiments, administration of the viral-loaded cyclodextrin to a subject results in a pH-dependent switch, releasing the viral particle from the cyclodextrin. In some embodiments, the pH can be adjusted, e.g., by a physician, pharmacist, or other healthcare provider, prior to administration to a subject, such that the viral particle is released from the cyclodextrin before administration to a subject.

In some embodiments, systems described herein use a buffer that changes pH in response to temperature changes. For example, at lower temperatures, the buffer remains more basic, promoting viral capsid polypeptides to bind to the interior of a cyclodextrin. At higher temperatures, the buffer becomes more acidic, promoting release of the virus from the cyclodextrin. The systems described herein can be used, e.g., to store liquid virus suspension as a cold yet not frozen liquid (e.g., at about $-20°$ C.) and then, prior to administration to a subject, the suspension can be warmed (e.g., to room temperature, namely, about $20°$ C. to about $25°$ C.), releasing the virus from the cyclodextrin.

In other embodiments, the systems described herein can be also be used to store the virus in a frozen state (e.g., such as in a freezer), as a frozen suspension, at temperatures less than or equal to $-60°$ C., about $-60°$ C. to about $-100°$ C., about $-60°$ C. to about $-90°$ C., about $-60°$ C. to about $-80°$ C., about $-60°$ C., about $-35°$ C. to about $-10°$ C., or about $-25°$ C. to about $-15°$ C. In some aspects, prior to administration to a subject, the composition containing the virus is thawed (e.g., by removal from a freezer), and brought to room temperature, namely, to a temperature of about $20°$ C. to about $25°$ C. Once the composition containing the virus is thawed, it can be stored as a liquid (e.g., a suspension), in a non-frozen state: (a) for up to 24 hours at room temperature; (b) at about $2°$ C. to about $8°$ C. (e.g., in a refrigerator) for up to 1 day, up to 2 days, up to 3 days, up to 4 days, up to 5 days, up to 6 days, or up to 7 days; (c) at about $2°$ C. to about $8°$ C. for up to 1 day, up to 2 days, up to 3 days, up to 4 days, up to 5 days, up to 6 days, or up to 7 days followed by up to 24 hours at room temperature; or (d) in a syringe for up to 1 hour, up to two hours, up to three hours, up to four hours, up to five hours or up to six hours.

As discussed herein, a temperature-responsive viral storage system of the disclosure was found to maintain viral infectivity when stored in liquid suspension for at least a full year. The disclosure thus provides, at least in part, a long-term preservation method for virus stored as a non-frozen liquid. The storage systems of the disclosure will be effective for a variety of medically-useful viruses, including, e.g., infectious adenovirus, Lentivirus and adeno-associated virus, viral vaccines made from such viruses, and recombinant versions of such viruses, in which the virus is stored in liquid form yet nonetheless maintains a high percentage of its original infectivity.

System Components

Temperature-responsive systems of the disclosure can include a cyclodextrin, a buffer, Tris, and various other components.

Cyclodextrin

Cyclodextrins are a known family of cyclic oligosaccharides, consisting of a macrocyclic ring of glucose subunits joined by α-1,4 glycosidic bonds. Cyclodextrins are produced from starch by enzymatic conversion. Cyclodextrins, as they are known today, were called "cellulosine" when first described by A Villiers in 1891. Soon after, F. Schardinger identified the three naturally occurring cyclodextrins -α, -β, and -γ. These compounds were therefore referred to as Schardinger sugars. For 25 years, between 1911 and 1935, Pringsheim in Germany was the leading researcher in this area, demonstrating that cyclodextrins formed stable aqueous complexes with many other chemicals. Cyclodextrins have a donut shaped structure, and the interior donut hole or cavity can house or encapsulate other compounds. Thus, extensive work has been conducted exploring encapsulation by cyclodextrins and their derivatives for industrial and pharmacologic applications. The prior art teaches that among the processes used for complexation, the "kneading" process is one of the best. Notably, however, systems of the disclosure do not require this.

Cyclodextrins are composed of 5 or more α-D-glucopyranoside units linked 1->4, as in amylose (a fragment of starch). Typical cyclodextrins contain a number of glucose monomers ranging from six to eight units in a ring, creating a cone shape, with β (beta)-cyclodextrin containing 7 glucose subunits. The largest currently-known, well-characterized cyclodextrin contains 32 1,4-anhydroglucopyranoside units, while as a poorly characterized mixture, at least 150-membered cyclic oligosaccharides are also known. In some embodiments, a cyclodextrin is a hydroxypropyl beta-cyclodextrin (e.g., CAS Registry No. 128446-35-5).

With a hydrophobic interior and hydrophilic exterior, cyclodextrins form complexes with hydrophobic compounds. Alpha-, beta-, and gamma-cyclodextrin are all generally recognized as safe by the U.S. FDA. They have been applied for delivery of a variety of drugs, including hydrocortisone, prostaglandin, nitroglycerin, itraconazol, chloramphenicol. The cyclodextrin confers solubility and stability to these drugs. The inclusion compounds of cyclodextrins with hydrophobic molecules are able to penetrate body tissues, these can be used to release biologically active compounds under specific conditions.

In contrast to these various known uses of cyclodextrins, our systems include cyclodextrin for an entirely new use: to protect an infective virus from reduction by a more-basic pH storage buffer until the buffer is warmed, increasing the buffer pH. This leads to controlled degradation of the virus-cyclodextrin complex due to the pH change of the buffer solution, leading to the loss of hydrogen or ionic bonding between the cyclodextrin and the viral capsid polypeptides. Without intending to be bound by theory, this system may sequester the virus inside the interior of the cyclodextrin during storage, and releases the virus from the cyclodextrin complex when the formulation is warmed, e.g., prior to administration to a patient.

In some embodiments, one virus particle may have many cyclodextrin molecules bound to it. For example, one or more viral spike peplomers on the surface of a virus can each bind to one or more cyclodextrin molecules. To assure that there are adequate cyclodextrin molecules to protect the virus particles, some preferred embodiments of systems described herein include far more cyclodextrin molecules than viral particles, e.g., from about $1 \times 10^6$ to about $1 \times 10^{12}$, from about $1 \times 10^7$ to about $1 \times 10^{12}$, from about $1 \times 10^8$ to about $1 \times 10^{12}$, from about $1 \times 10^9$ to about $1 \times 10^{12}$ (e.g., about $1 \times 10^6$, about $1 \times 10^7$, about $1 \times 10^8$, about $1 \times 10^9$, about $1 \times 10^{10}$, about $1 \times 10^{11}$, or about $1 \times 10^{12}$) cyclodextrin molecules per viral particle.

Buffer

Systems of the disclosure include a buffer solution similar to Mellvaine buffer. Mellvaine buffer is a buffer solution composed of citric acid and disodium hydrogen phosphate, also known as citrate-phosphate buffer. It was invented in 1921 by a United States agronomist (Theodore Clinton Mellvaine from West Virginia University). It can be prepared in pH 2.2 to 8 by mixing two stock solutions. Mellvaine buffer can be used to prepare a water-soluble mounting media when mixed 1:1 with glycerol. While preparation of Mellvaine buffer requires disodium phosphate and citric acid, buffers for the systems of the disclosure replace disodium phosphate with monosodium phosphate (dihydrate).

Monosodium phosphate (dihydrate) is also known as sodium dihydrogen phosphate dehydrate (CAS Registry Number: 13472-35-0), sodium phosphate monobasic dehydrate and monosodium dihydrogen phosphate dehydrate. It is often used as an emulsifier, thickening agent, for softening water, and as an efficient anti rust solution. In systems of the disclosure, monosodium phosphate (dihydrate) can control pH when included as part of a buffer.

Citric acid is a weak organic acid that has the chemical formula $C_6H_8O_7$. It occurs naturally in citrus fruits. In biochemistry, it is an intermediate in the citric acid cycle, which occurs in the metabolism of all aerobic organisms. It is used widely as an acidifier, anti-oxidant, flavoring and chelating agent. The term "citrate" is used herein as it is conventionally used in the art, to denote a derivative of citric acid, that is the salts, esters, and the polyatomic anion found in solution. For example, an exemplary citrate salt is trisodium citrate; a citrate ester is triethyl citrate. When part of a salt, the formula of the citrate ion is written as $C_6H5O^{3-}{}_7$ or $C_3H_5O(COO)^{3-}{}_3$. In some embodiments, systems of the disclosure include citric acid monohydrate.

One liter of 0.2M stock solution of disodium phosphate can be prepared, e.g., by dissolving 0.2 moles of monosodium phosphate (dihydrate) in water, and adding a quantity of water sufficient to make one liter. One liter of 0.1M stock solution of citric acid can be prepared, e.g., by dissolving 0.1 moles (19.21 gms) of citric acid in water, and adding a quantity of water sufficient to make one liter. In some embodiments, monosodium phosphate (dihydrate) and citric acid are used at a ratio of about 1.7: about 0.01. In some embodiments, monosodium phosphate (dihydrate) and citric acid are used at a ratio of from about 1.5: about 0.01, to about 2.0: about 0.01.

Buffers described herein can also include sodium citrate dihydrate. Sodium citrate dehydrate is used as an emulsifier in foods, and also as an anti-coagulant to prevent donated blood from clotting in storage. In some embodiments, sodium citrate dehydrate is included and functions as a pH regulator in conjunction with citric acid.

Buffers described herein can also include magnesium chloride. Magnesium chloride can refer to either the chemical compound with the formula $MgCl_2$ or its various hydrates $MgCl_2(H_2O_x)$. The hydrated magnesium chloride can be extracted from brine or sea water. Some magnesium chloride is made from solar evaporation of seawater. In some embodiments, magnesium chloride is MgCl hexahydrate. Magnesium chloride is known and commercially available (e.g., USP, CAS Registry No. 7791-18-6).

Tris

Systems of the disclosure include Tris to impart temperature-dependent pH shifting properties. Tris, also known as tris(hydroxymethyl)aminomethane, tromethamine or THAM, is an organic compound with the formula $(HOCH_2)_3CNH_2$. It contains a primary amine and thus undergoes the reactions associated with typical amines, e.g., condensations with aldehydes. In medicine, tromethamine is occasionally used as a drug, given in intensive care for the treatment of severe metabolic acidosis in specific circumstances. Some medications are formulated as the tromethamine salt. These include hemabate (carboprost as the trometamol salt), and ketorolac trometamol. In systems of the disclosure, Tris buffer causes pH to decrease as the formulation changes temperature from a lower temperature to a higher temperature (e.g., is removed from cold storage and warmed (e.g., to room temperature or body temperature)), e.g., prior to administration to a subject. In some embodiments, the pH change is an average of about 0.03 units pH per degree Celsius, e.g., as temperature increases from 5 degrees Celsius to 25 degrees Celsius.

In some embodiments, temperature-dependent pH shifting properties are based on a ratio of Tris to sodium phosphate. In some embodiments, systems of the disclosure include a molar ratio of Tris to sodium phosphate of about 0.5 to about 2 moles of Tris per mole of sodium phosphate (e.g., about 1 to about 1.5 moles of Tris per mole of sodium phosphate, e.g., about 1 mole of Tris per mole of sodium phosphate, about 1.25 moles of Tris per mole of sodium phosphate, or about 1.5 moles of Tris per mole of sodium phosphate).

Additional Components

In some embodiments, systems of the disclosure include polysorbate 80 (Tween 80). Polysorbate 80 is a non-ionic surfactant and emulsifier often used in foods, cosmetics and for vaccine suspensions to assure regular distribution of the virus in the buffer. This synthetic compound is a viscous, water-soluble yellow liquid. Polysorbate 80 is an excipient that is used to stabilize aqueous formulations of medications for parenteral administration, and used as an emulsifier in the making of the popular anti-arrhythmic drug amiodarone. It is also used as an excipient in some European and Canadian influenza vaccines. Commercially-available influenza vaccines, for example, contain 2.5 μg of polysorbate 80 per dose. It is also used in the culture of *Mycobacterium tuberculosis* in Middlebrook 7H9 broth. It is also used as an emulsifier in the estrogen-regulating drug Estrasorb, and used in granulation for stabilization of drug and excipients while doing IPA (isopropyl alcohol) binding.

In some embodiments, systems of the disclosure include one or more art-known cryo-protectants. In some embodiments, inclusion of a cryo-protectant allows a virus suspension to be frozen, if desired and/or required. One example of a cryo-protectant is glycerol. Also called glycerin, it is a simple polyol compound. It is a colorless, odorless, viscous liquid that is sweet-tasting and non-toxic. The glycerol backbone is found in those lipids known as glycerides. Due to having antimicrobial and antiviral properties it is widely used in FDA approved wound and burn treatments. It can also be used as an effective marker to measure liver disease. It is also widely used as a sweetener in the food industry and as a humectant in pharmaceutical formulations. Owing to the presence of three hydroxyl groups, glycerol is miscible with water and is hygroscopic in nature.

In some embodiments, systems of the disclosure include sucrose (common sugar) as a cryo-protectant. It is a disaccharide, a molecule composed of two mono-saccharides: glucose and fructose. Sucrose is produced naturally in plants, from which table sugar is refined. It has the molecular formula $C_{12}H_{22}O_{11}$.

In some embodiments, systems of the disclosure include a steroid-like phenanthrene derivative, (3α, 5β, 7α, 12α)-N-[3-[(4-O-D-galactopyranosyl-D-gluconoyl)amino]propyl]-3,7,12-trihydroxy-N-[3-[[(3α, 5β, 7α, 12α]-3,7,12-trihydroxy-24-oxocholan-24-yl]amino]propyl]-cholan-24-amide, CAS Registry No. 2127497-44-5, also commonly known as NODA (see, e.g., WO 2017/180344; WO 2005/058368; U.S. Pat. No. 6,392,069). NODA is known to aid viral penetration of muco-polysaccharide coatings. Accordingly, in some embodiments where the virus is to be administered to a muco-polysaccharide-coated body part, NODA is included.

Exemplary Temperature-Responsive Virus Storage Systems

In some embodiments, a storage system of the disclosure comprises an initial formulation that includes the following components, with the amount of each component expressed as a percent of the weight (w/w) of Tris(tromethamine): about 5,000% to about 7,000% glycerol; about 900% to about 1,300% sucrose; about 100% tromethamine; about 75% to about 125% Na dihydrogen phosphate dehydrate; about 500% to about 700% hydroxypropyl beta-cyclodextrin; about 10% to about 30% MgCl hexahydrate; 0% to about 100% NODA; about 20% to about 50% polysorbate 80; about 1% to about 4% sodium citrate dehydrate; and about 0.5% to about 2% citric acid monohydrate. In some embodiments, a storage system of the disclosure comprises one part of the initial formulation and about 7, 8, 9, 10, 11, or 12 parts of water.

In some embodiments, a storage system of the disclosure comprises an initial formulation that includes the following components, with the amount of each component expressed as a percent of the weight (w/w) of Tris(tromethamine): about 4,500%, about 5,000%, about 5,500%, about 6,000%, about 6,500%, about 7,000%, or about 7,500% glycerol; about 800%, about 900%, about 1,000%, about 1,100%, about 1,200%, about 1,300%, or about 1,400% sucrose; about 100% tromethamine; about 65%, about 75%, about 85%, about 95%, about 100%, about 105%, about 115%, or about 125% Na dihydrogen phosphate dehydrate; about 400%, about 500%, about 550%, about 560%, about 575%, about 580%, about 590%, about 600%, about 700%, or about 800% hydroxypropyl beta-cyclodextrin; about 5%, about 10%, about 15%, about 20%, about 21%, about 22%, about 25%, about 30%, about 35%, or about 40% MgCl hexahydrate; 0%, about 10%, about 20%, about 25%, about 30%, about 35%, about 40%, about 45%, about 50%, about 55%, about 60%, about 65%, about 70%, about 75%, about 80%, about 85%, about 90%, about 95%, or about 100% NODA; about 10%, about 20%, about 25%, about 30%, about 35%, about 40%, about 50%, or about 60% polysorbate 80; about 0.5%, about 1%, about 2%, about 3%, about 4%, or about 5% sodium citrate dehydrate; and about 0.25%, about 0.5%, about 1%, about 1.5%, about 2%, about 2.5%, or about 3% citric acid monohydrate. In some embodiments, a storage system of the disclosure comprises one part of the initial formulation and about 7, 8, 9, 10, 11, or 12 parts of water.

In some other embodiments, a storage system of the disclosure comprises an initial formulation that includes the following components, with the amount of each component expressed as a percent of the weight (w/w) of Tris(tromethamine): from about 5,800% to about 6100% glycerol; from about 1200% to about 1225% sucrose; from about 95% to about 105% tromethamine; from about 95% to about 110% Na dihydrogen phosphate dehydrate; from about 550% to about 600% hydroxypropyl beta-cyclodextrin; from about 25% to about 35% MgCl hexahydrate; from about 65% to about 75% NODA; from about 30% to about 40% polysorbate 80; from about 2% to about 3% sodium citrate dehydrate; and about 0.50% to about 1% citric acid monohydrate. In some embodiments, a storage system of the disclosure comprises one part of the initial formulation and about 7, 8, 9, 10, 11, or 12 parts of water. Additionally, in some aspects, the formulation can further contain about $3 \times 10^{11}$ vp/mL of nadofaragene firadenovec.

In yet other embodiments, a storage system of the disclosure comprises an initial formulation that includes the following components, with the amount of each component expressed as a percent of the weight (w/w) of Tris(tromethamine): about 6,000% glycerol; about 1214% sucrose; about 100% tromethamine; about 100% Na dihydrogen phosphate dehydrate; from about 560% hydroxypropyl beta-cyclodextrin; about 29% MgCl hexahydrate; about 68% NODA; about 34% polysorbate 80; from about 2.8% sodium citrate dehydrate; and about 0.71% citric acid monohydrate. In some embodiments, a storage system of the disclosure comprises one part of the initial formulation and about 7, 8, 9, 10, 11, or 12 parts of water. Additionally, in some aspects, the formulation can further contain about $3 \times 10^{11}$ vp/mL of nadofaragene firadenovec.

In some embodiments, a storage system of the disclosure comprises an initial formulation that includes the following components, with the amount of each component expressed as a percent of the weight (w/w) of Tris(tromethamine): about 6,000% glycerol; about 1,200% sucrose; about 100% tromethamine; about 100% Na dihydrogen phosphate dehydrate; about 600% hydroxypropyl beta-cyclodextrin; about 20% MgCl hexahydrate; 0% NODA; about 35% polysorbate 80; about 3% sodium citrate dehydrate; and about 0.75% citric acid monohydrate. In some embodiments, a storage system of the disclosure comprises one part of the initial formulation and about 7, 8, 9, 10, 11, or 12 parts of water. Additionally, in some aspects, the formulation can further contain about $3 \times 10^{11}$ vp/mL of nadofaragene firadenovec.

In some embodiments, a storage system of the disclosure comprises an initial formulation that includes the following components, with the amount of each component expressed as a percent of the weight (w/w) of Tris(tromethamine): about 4,000% glycerol; about 700% sucrose; about 100% tromethamine; about 150% Na dihydrogen phosphate dehydrate; about 400% hydroxypropyl beta-cyclodextrin; about 60% MgCl hexahydrate; about 75% NODA; about 90% polysorbate 80; about 6% sodium citrate dehydrate; and about 3% citric acid monohydrate. In some embodiments, a storage system of the disclosure comprises one part of the initial formulation and about 7, 8, 9, 10, 11, or 12 parts of water. Additionally, in some aspects, the formulation can further contain about $3 \times 10^{11}$ vp/mL of nadofaragene firadenovec.

In some embodiments, a storage system of the disclosure comprises an initial formulation that includes the following components, with the amount of each component expressed as a percent of the weight (w/w) of Tris(tromethamine): about 6,000% glycerol; about 1,200% sucrose; about 100% tromethamine; about 100% Na dihydrogen phosphate dehydrate; about 590% hydroxypropyl beta-cyclodextrin; about 21% MgCl hexahydrate; about 71% NODA; about 36% polysorbate 80; about 3% sodium citrate dehydrate; and about 1% citric acid monohydrate. In some embodiments, a storage system of the disclosure comprises one part of the initial formulation and about 7, 8, 9, 10, 11, or 12 parts of water. Additionally, in some aspects, the formulation can further contain about $3 \times 10^{11}$ vp/mL of nadofaragene firadenovec.

In some embodiments, a storage system of the disclosure comprises an initial formulation that includes the following components, with the amount of each component expressed as a percent of the weight (w/w) of Tris(tromethamine): about 92% Sodium phosphate, about 100% Tris, about 11% Magnesium chloride, about 1,180% sucrose, about 5,900% glycerol. In some embodiments, a storage system of the disclosure comprises one part of the initial formulation and about 7, 8, 9, 10, 11, or 12 parts of water. Additionally, in some aspects, the formulation can further contain about $3 \times 10^{11}$ vp/mL of nadofaragene firadenovec.

In some embodiments, systems of the disclosure exhibit a pH shift of about 0.03 units pH per degree Celsius, e.g., as temperature increases from 5 degrees Celsius to 25 degrees Celsius.

Viruses

Systems of the disclosure can include any type of virus, e.g., viral vector, e.g., a viral vector for gene therapy. A number of viral based systems have been developed for gene transfer into mammalian cells. Examples of viral vectors include, but are not limited to, retroviruses, adenoviruses, adeno-associated viruses, herpes viruses, lentiviruses, poxviruses, herpes simplex 1 virus, herpes virus, oncoviruses (e.g., murine leukemia viruses), and the like. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Retroviruses are enveloped viruses that belong to the viral family Retroviridae. Once in a host's cell, the virus replicates by using a viral reverse transcriptase enzyme to transcribe its RNA into DNA. The retroviral DNA replicates as part of the host genome, and is referred to as a provirus. A transgene can be inserted into a vector and packaged in retroviral particles using techniques known in the art. The recombinant virus can then be isolated and delivered to cells of the subject either in vivo or ex vivo. A number of retroviral systems are known in the art, for example see, U.S. Pat Nos. 5,994,136, 6,165,782, and 6,428,953.

Retroviruses include the genus of Alpharetrovirus (e.g., avian leukosis virus), the genus of Betaretrovirus; (e.g., mouse mammary tumor virus) the genus of Deltaretrovirus (e.g., bovine leukemia virus and human T-lymphotropic virus), the genus of Epsilonretrovirus (e.g., Walleye dermal sarcoma virus), and the genus of Lentivirus.

In some embodiments, the retrovirus is a Lentivirus a genus of viruses of the Retroviridae family, characterized by a long incubation period. Lentiviruses are unique among the retroviruses in being able to infect non-dividing cells; they can deliver a significant amount of genetic information into the DNA of the host cell, so they are one of the most efficient methods of a gene delivery vector. Lentiviral vectors have an advantage to other viral vectors in that they can transduce non-proliferating cells and show low immunogenicity. In some examples, the Lentivirus includes, but is not limited to human immunodeficiency viruses (HIV-1 and HIV-2), simian immunodeficiency virus (SIV), feline immunodeficiency virus (FIV), equine infections anemia (EIA), and visna virus. Vectors derived from lentiviruses offer the means to achieve significant levels of gene transfer in vivo.

In embodiments, the vector is an adenovirus vector. Adenoviruses are a large family of viruses containing double stranded DNA. They replicate the DNA of the host cell, while using the host's cell machinery to synthesize viral RNA, DNA and proteins. Adenoviruses are known in the art to affect both replicating and non-replicating cells, to accommodate large transgenes, and to code for proteins without integrating into the host cell genome.

In some embodiments, the viral vector is an adeno-associated virus (AAV) vector. AAV systems are generally well known in the art (see, e.g., Kelleher and Vos, *Biotechniques*, 17(6): 1110-17 (1994); Cotten et al., *P.N.A.S. U.S.A.*, 89 (13): 6094-98 (1992); Curiel, *Nat Immun.*, 13(2-3): 141-64 (1994); Muzyczka, *Curr Top Microbiol Immunol.*, 158:97-129 (1992); and Asokan A, et al., *Mol. Ther.*, 20 (4): 699-708 (2012)). Methods for generating and using recombinant AAV (rAAV) vectors are described, for example, in U.S. Pat. Nos. 5,139,941 and 4,797,368. Several AAV serotypes have been characterized, including AAV1, AAV2, AAV3 (e.g., AAV3B), AAV4, AAV5, AAV6, AAV7, AAV8, AAV9, AAV10, and AAV11, as well as variants thereof.

Transgenes

A system of the disclosure can include a virus described herein that includes or encodes any transgene of interest. In some embodiments, a virus includes or encodes type 1 and/or type 2 interferons, including deletion, insertion, or substitution variants thereof, biologically active fragments, and allelic forms. Type 1 interferons include interferon-α, -β, -ε, -κ, -Ω, -δ, -ζ, -τ and their subtypes, while Type 2 interferons are referred to as interferon-γ (see, e.g., Lee et al., *Front. Immunol.*, 9:2061 (2018)). Particular interferon-α's include human interferon α subtypes including, but not limited to, α-1 (GenBank Accession Number NP 076918), α-1b (GenBank Accession Number AAL35223), α-2, α-2a (GenBank Accession Number NP000596), α-2b (GenBank Accession Number AAP20099), α-4 (GenBank Accession Number NP066546), α-4b (GenBank Accession Number CAA26701), α-5 (GenBank Accession Numbers NP 002160 and CAA26702), α-6 (GenBank Accession Number CAA26704), α-7 (GenBank Accession Numbers NP 066401 and CAA 26706), α-8 (GenBank Accession Numbers NP002161 and CAA 26903), α-10 (GenBank Accession Number NP 002162), α-13 (GenBank Accession Numbers NP 008831 and CAA 53538), α-14 (GenBank Accession Numbers NP 002163 and CAA 26705), α-16 (GenBank Accession Numbers NP 002164 and CAA 26703), a α-17 (GenBank Accession Number NP 067091), α-21 (GenBank Accession Numbers P01568 and NP002166), and consensus interferons as described in U.S. Pat. Nos. 5,541,293; 4,897,471; and 4,695,629; and hybrid interferons as described in U.S. Pat. No. 4,414,150. Interferon-γ's are described in, e.g., EP 77,670A and EP 146,354A, and GenBank Accession Number NP 002168. Particular compositions of the disclosure comprise a recombinant adenoviral vector encoding an interferon-a described in U.S. Pat. No. 6,835,557, e.g., with or without a signal sequence. In some embodiments, a non-replicating recombinant adenoviral vector comprises or is a type 5 non-replicating adenoviral vector. In some embodiments, a non-replicating recombinant adenoviral vector is a recombinant adenoviral vector described in, e.g., U.S. Pat. No. 6,210,939. In some embodiments, a recombinant adenoviral vector encodes at least one IFN α-2 (e.g., one or both of IFN α-2a or IFN α-2b). In certain embodiments, a recombinant adenoviral vector encodes human IFN α-2b.

Storage of Viral Particles

Systems of the disclosure can be used to store formulations that include viral particles (e.g., viral vector particles). In some embodiments, a viral vector (e.g., an adenoviral vector, e.g., an adenoviral vector encoding interferon α-2b) is formulated using a system of the disclosure and is subjected to storage conditions, e.g., stored frozen or non-frozen (e.g., less than or equal to about −60° C., about −60° C. to about −100° C., about −60° C. to about −90° C., about −60° C. to about −80° C., about −60° C., about −35° C. to about −10° C., or about −25° C. to about −15° C., at about −5° C., at about 0° C., at about at 4° C., or at about at 8° C.) for about 1 month, 2 months, 3 months, 4 months, 5 months, 6 months, 7 months, 8 months, 9 months, 10 months, 11 months, 12 months, 14 months, 16 months, 18 months, 20 months, 22 months, 24 months, 28 months, 32 months, 36 months, 48 months, or longer. In some embodiments, after storage at such storage conditions, the viral vector maintains a high level of infectivity, relative to control. For example, after storage at such storage conditions, the viral vector demonstrates a level of infectivity that is at least about 50%, 60%, 70%, 80%, 85%, 90%, 95%, or more, relative to a control level of infectivity (e.g., level of infectivity of such viral vector before storage at such storage conditions, or level of infectivity of such viral vector at a prior time during such storage conditions). In some embodiments, after storage at such storage conditions, the viral vector demonstrates a level of infectivity that is reduced by no more than about 40%, 35%, 30%, 25%, 20%, 15%, 10%, 5% or less, relative to a control level of infectivity (e.g., level of infectivity of such viral vector before storage at such storage conditions, or level of infectivity of such viral vector at a prior time during such storage conditions).

In some embodiments, a viral vector (e.g., an adenoviral vector, e.g., an adenoviral vector encoding interferon α-2b) is formulated using a system of the disclosure and is subjected to storage conditions, e.g., stored frozen or non-frozen (e.g., less than or equal to about −60° C., about −60° C. to about −100° C., about −60° C. to about −90° C., about −60° C. to about −80° C., about −60° C., about −35° C. to about −10° C., or about −25° C. to about −15° Cat about −5° C., at about 0° C., at about at 4° C., or at about at 8° C.) for about 1 month, 2 months, 3 months, 4 months, 5 months, 6 months, 7 months, 8 months, 9 months, 10 months, 11 months, 12 months, 14 months, 16 months, 18 months, 20 months, 22 months, 24 months, 28 months, 32 months, 36 months, 48 months, or longer. In some embodiments, after storage at such storage conditions, the formulation maintains a high level of total viral particle concentration, relative to control. For example, after storage at such storage conditions, level of total viral particle concentration is at least about 70%, 80%, 85%, 90%, 95%, or more, relative to a control level of total viral particle concentration (e.g., level of total viral particle concentration before storage at such storage conditions, or level of total viral particle concentration at a prior time during such storage conditions). In some embodiments, after storage at such storage conditions, the level of total viral particle concentration is reduced by no more than about 30%, 25%, 20%, 15%, 10%, 5% or less, relative to a control level of total viral particle concentration (e.g., level of total viral particle concentration before storage at such storage conditions, or level of total viral particle concentration at a prior time during such storage conditions).

Methods and assays for measuring viral particle concentration and infectivity are known in the art. See, e.g., Nyberg-Hoffman et al., Nat. Med., 3:808-11 (1997); Barde et al., Curr. Protoc. Neurosci., 53:4.21.1-4.21.23 (2010); Pankaj, Mater. Methods, 3:207 (2013); WO2017/048599. In some embodiments, a sample of a viral vector stored under storage conditions described herein is brought to room temperature (e.g., held at room temperature for about 15 minutes, 30 minutes, 45 minutes, 1 hour, 2 hours, 4 hours, or longer), before measuring viral particle concentration or infectivity. As known in the art, level of infectivity can be expressed, e.g., as NAS IU (Normalized and Adjusted Standard-Infectious Units) per mL.

Compositions and Administration

A system described herein (e.g., a composition comprising system components and a viral vector described herein) can be formulated into a pharmaceutical composition. Such a pharmaceutical composition can be useful, e.g., for the prevention and/or treatment of diseases, e.g., cancer (e.g., bladder cancer). In some embodiments, a pharmaceutical composition can be formulated to include a pharmaceutically acceptable carrier or excipient.

In some embodiments, a composition described herein can be formulated as a sterile formulation for injection in accordance with conventional pharmaceutical practices. In some embodiments, a composition described herein is a sterile suspension formulation for intravesical instillation.

In some embodiments, a pharmaceutical compositions described herein is substantially free of contaminants (e.g., components (e.g., DNA and protein) of host cells (e.g., HEK293 cells) and/or serum (e.g., fetal bovine serum)). In some embodiments, a pharmaceutical composition described herein comprises trace amounts of contaminants (e.g., components (e.g., DNA and protein) of host cells (e.g., HEK293 cells) and/or serum (e.g., fetal bovine serum)). In some embodiments, a pharmaceutical composition described herein is substantially free of preservative.

Selection or use of any particular form may depend, in part, on the intended mode of administration and therapeutic application. For example, compositions intended for systemic or local delivery can be in the form of injectable or infusible solutions. Accordingly, compositions can be formulated for administration by a parenteral mode (e.g., intravenous, subcutaneous, intraperitoneal, or intramuscular injection). As used herein, parenteral administration refers to modes of administration other than enteral and topical administration, usually by injection, and include, without limitation, intravesical, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion. Administration can be systemic or local. Route of administration can be parenteral, for example, administration by intravesical instillation or injection. In some embodiments, intravesical administration can be accomplished by means of a device, such as a catheter.

As discussed herein, a system described herein can be formulated with a viral vector for storage under storage conditions described herein. In some embodiments, a composition is stored frozen (e.g., at a temperature less than or equal to about −60° C., about −60° C. to about −100° C., about −60° C. to about −90° C., about −60° C. to about −80° C., about −60° C., about −35° C. to about −10° C., or about −25° C. to about −15° C.) and is thawed at room temperature (e.g., about 20° C. to about 25° C.) until liquid prior to administration to a subject. Once the composition is thawed, it can be stored as a liquid (e.g., a suspension), in a non-frozen state: (a) for up to 24 hours at room temperature; (b) at about 2° C. to about 8° C. (e.g., in a refrigerator) for up to 1 day, up to 2 days, up to 3 days, up to 4 days, up to 5 days, up to 6 days, or up to 7 days; or (c) at about 2° C. to about 8° C. for up to 1 day, up to 2 days, up to 3 days, up to 4 days, up to 5 days, up to 6 days, or up to 7 days followed by up to 24 hours at room temperature.

In some embodiments, a composition is stored non-frozen and is warmed to room temperature (e.g., about 20° C. to about 25° C.) prior to administration to a subject. In some embodiments, a composition is warmed to room temperature, and maintained at room temperature for about 15 minutes, 30 minutes, 45 minutes, 1 hour, 2 hours, 4 hours, or longer, before administration to a subject.

In some embodiments, once the composition is warmed to room temperature (e.g., about 20° C. to about 25° C.), it may be placed in a syringe prior to administration to a subject. The composition can be placed or stored as a liquid in a syringe for at least one hour, at least two hours, at least three hours, at least four hours, at least five hours, or up to at least six hours prior to administration to a subject. In some aspects, the composition can be placed or stored as a liquid in a syringe for up to about six hours prior to administration to a subject.

The pharmaceutical compositions described herein can be used to treat a subject. The compositions described herein can be used, for example, to treat or prevent a cancer (e.g., a cancer, e.g., a carcinoma or other solid or hematological cancer, a cancer metastases). As used herein, the term "cancer" is meant to include all types of cancerous growths or oncogenic processes, metastatic tissues or malignantly transformed cells, tissues, or organs, irrespective of histopathologic type or stage of invasiveness. Methods and compositions disclosed herein are particularly useful for treating, or reducing the size, numbers, or rate of growth of, metastatic lesions associated with cancer.

Examples of cancers include, but are not limited to, solid tumors, soft tissue tumors, hematopoietic tumors and metastatic lesions. Examples of solid tumors include malignancies, e.g., sarcomas, adenocarcinomas, and carcinomas, of the various organ systems, such as those affecting head and neck (including pharynx), thyroid, lung (small cell or non-small cell lung carcinoma), breast, lymphoid, gastrointestinal (e.g., oral, esophageal, stomach, liver, pancreas, small intestine, colon and rectum, anal canal), genitals and genitourinary tract (e.g., renal, urothelial, bladder, ovarian, uterine, cervical, endometrial, prostate, testicular), CNS (e.g., neural or glial cells, e.g., neuroblastoma or glioma), skin (e.g., melanoma). Examples of hematopoietic cancers that can be treated include hemangiomas, multiple myeloma, lymphomas and leukemias and myelodysplasia. Methods and compositions disclosed herein are particularly useful for treating, e.g., reducing or delaying, metastatic lesions associated with the aforementioned cancers. In some embodiments, a subject will have undergone one or more of surgical removal of a tissue, chemotherapy, or other anti-cancer therapy and the primary or sole target will be metastatic lesions, e.g., metastases in the bone or lymph nodes or lung or liver or peritoneal cavity or the CNS or other organs.

Those of skill in the art will appreciate that data obtained from cell culture assays and animal studies can be used in formulating a range of dosage for use in humans. Appropriate dosages of compositions described herein lie generally within a range of circulating concentrations of the compositions that include the $ED_{50}$ with little or no toxicity. A dosage may vary within this range depending upon the dosage form employed and route of administration utilized. For a composition described herein, a therapeutically effective dose can be estimated initially from cell culture assays. A dose can be formulated in animal models to achieve a circulating plasma concentration range that includes an $IC_{50}$ as determined in cell culture. Such information can be used to more accurately determine useful doses in humans. Levels in plasma may be measured, for example, by high performance liquid chromatography. In some embodiments, e.g., where local administration (e.g., to bladder tissue) is desired, cell culture or animal modeling can be used to determine a dose required to achieve a therapeutically effective concentration within a local site.

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

The disclosure is further illustrated by the following examples. The examples are provided for illustrative purposes only. They are not to be construed as limiting the scope or content of the disclosure in any way.

EXAMPLES

Example 1 provides an exemplary range of weights for each ingredient, with the amount of each component expressed as a percent of the weight of Tris(tromethamine) used to make the composition.

TABLE 1

| formula | |
|---|---|
| Ingredient | Amount (w/w) |
| glycerol | 5,000- |
| sucrose | 900- |
| tromethamine | 100% |
| Na dihydrogen phosphate dihydrate | 75-125% |
| hydroxypropyl beta-cyclodextrin | 500-700% |
| MgCl hexahydrate | 10- |
| NODA | 0- |
| polysorbate 80 | 20- |
| sodium citrate dihydrate | 1-4% |
| citric acid monohydrate | 0.5-2% |

One combines one part (w/w) of this with about 10 parts (w/w) purified water to make the final buffer. This buffer then is used to suspend infective virus. The density of virus in the buffer depends on the ultimate medical use of the virus. Vaccines and other injectable products would call for a more concentrated preparation (less volume of buffer to virus). Irrigation products for e.g., bladder instillation or thoracic irrigation could use a more dilute preparation, e.g., from about $1\times10^{10}$ to about $1\times10^{13}$ viral particles per mL of buffer. In this Example, one uses $4\times10^{16}$ lentiviral particles per mL.

Example 2

An exemplary buffer is shown here in Table 2, with the amount of each component expressed as a percent of the weight of Tris(tromethamine) used to make the composition.

TABLE 2

| formula | |
|---|---|
| Ingredient | Amount (w/w) |
| glycerol | 6,000% |
| sucrose | 1,200% |
| tromethamine | 100% |
| Na dihydrogen phosphate dihydrate | 100% |
| hydroxypropyl beta-cyclodextrin | 600% |
| magnesium chloride hexahydrate | 20% |
| NODA | 0% |
| polysorbate 80 (Tween 80) | 35% |
| sodium citrate dihydrate | 3% |
| citric acid monohydrate | 0.75% |

One combines one part (w/w) of this with nine parts (w/w) purified water to make the final buffer. This buffer then is used to suspend infective virus at a concentration of about $1\times10^{11}$ adeno-associated viral particles per mL of buffer.

Example 3

Another exemplary buffer is shown here in Table 3, with the amount of each component expressed as a percent of the weight of Tris(tromethamine) used to make the composition.

TABLE 3

| formula | |
|---|---|
| Ingredient | Amount (w/w) |
| glycerol | 4,000% |
| sucrose | 700% |
| tromethamine | 100% |
| Na dihydrogen phosphate dihydrate | 150% |
| hydroxypropyl beta-cyclodextrin | 400% |
| magnesium chloride hexahydrate | 60% |
| NODA | 75% |
| polysorbate 80 | 90% |
| sodium citrate dihydrate | 6% |
| citric acid monohydrate | 3% |

One combines one part (w/w) of this with nine parts (w/w) purified water to make the final buffer. This buffer then is used to suspend infective virus at a concentration of about $3\times10^{11}$ adenoviral particles per mL of buffer.

Example 4

Another exemplary buffer is shown here as Table 4, with the amount of each component expressed as a percent of the weight of Tris(tromethamine) used to make the composition.

TABLE 4 formula

| Ingredient | Amount (w/w) |
|---|---|
| glycerol | 6,000% |
| sucrose | 1,200% |
| tromethamine | 100% |
| Na dihydrogen phosphate dihydrate | 100% |
| hydroxypropyl beta-cyclodextrin | 590% |
| magnesium chloride hexahydrate | 21% |
| NODA | 71% |
| polysorbate 80 (Tween 80) | 36% |
| sodium citrate dihydrate | 3% |
| citric acid monohydrate | 1% |

One combines one part (w/w) of this with nine parts (w/w) purified water to make the final buffer. This buffer then is used to suspend infective virus at a concentration of about $3 \times 10^{11}$ adenoviral particles per mL of buffer.

We have tested our buffer and found that it preserves infectivity of virus even when the suspended virus is stored as a non-frozen liquid, and so doing preserves infectivity for at least a full year.

Example 5

Another exemplary buffer is shown here in Table 5, with the amount of each component expressed as a percent of the weight of Tris(tromethamine) used to make the composition.

TABLE 5 formula

| Ingredient | Amount (w/w) |
|---|---|
| glycerol | 6,000% |
| sucrose | 1,214% |
| tromethamine | 100% |
| Na dihydrogen phosphate dihydrate | 100% |
| hydroxypropyl beta-cyclodextrin | 560% |
| magnesium chloride hexahydrate | 29% |
| NODA | 68% |
| polysorbate 80 (Tween 80) | 34% |
| sodium citrate dihydrate | 2.8% |
| citric acid monohydrate | 0.71% |

One combines one part (w/w) of this with nine parts (w/w) purified water to make the final buffer. This buffer then is used to suspend infective virus at a concentration of about $3 \times 10^{11}$ nadofaragene firadenovec particles per mL of buffer.

Example 6: Infectivity Assay Protocol

We assayed infectivity of virus samples using a fluorescence activated cell sorter (FACS).

For virus, we used a replication-deficient recombinant adenovirus type 5 (rAd). The assay principle is that HEK293 cells are infected with 30, 60 and 90 viral particles (vp) per cell (ppc) of rAd for 15 minutes and left to produce the virus for 48 hours. HEK293 cells contain complementation functions and thus enable a replication-deficient virus to replicate. After incubation, infected cells are fixed and stained with FITC conjugated antibody against adenovirus hexon structural protein. Hexon that has accumulated within infected cells can then be quantified with flow cytometer. As a second way to assay infectivity, we used rAd bearing a gene for interferon (rAd-IFN). Expression of this gene enabled us to measure interferon activity, a proxy for viral infectiveness.

All cell work and procedures up to fixing the cells were performed using aseptic techniques in a laminar flow hood to minimize biohazard risk to the operators. After fixing, the rest of the procedures before cytometer analysis, were performed in a fume hood.

The control sample rAd was formulated in final formulation buffer of 10.9 mM Sodium phosphate, 14 mM Tris base, 2 mM Magnesium chloride, 2% (w/v) sucrose, 10% (w/v) glycerol, which, at room temperature, provides a slightly basic pH of 8.1. We used a viral particle concentration of $5.4 \times 10^{11}$ vp/ml.

As a reference standard, we used purified rAd virus manufactured by Merck Sharpe & Dohme, Switzerland. The reference standard had a virus particle concentration of $1.4 \times 10^{12}$ vp/ml, an infectivity at the beginning of our testing of $1.37 \times 10^{11}$ NAS IU/ml ("NAS IU" is Normalized and Adjusted Standard-Infectious Units) and a potency of 251 IU/ml.

Infectivity assay for rAd process development samples can be run either using 6-well or 96-well plates, depending on the number of samples to be analyzed. Results were reported as a relative titer against reference standard, and assay performance was monitored using the control sample. On a 6-well plate assay, three test samples (TS), reference standard (RS) and a control sample (CS) can be analyzed. On a 96-well plate 15 test samples can be analyzed. If a comparison of the infectivity of different samples needs to be done, the samples should be analyzed in the same assay.

Our standard assay consisted of 20 wells, three full plates and two wells on the fourth. To do the assay, we first prepared a cell suspension that has $7.4 \times 10^5$ cells/ml. To do so, we pipette the calculated amount of pre-warmed growth medium to a sterile container. We then mixed the cell suspension gently but thoroughly by inverting at least 10 times before transferring the calculated amount of suspension to the container with growth media. We then mixed the seeding sell suspension thoroughly by pipetting up and down with a PIPETBOY® at least 10 times. We then seeded 1 ml/well on 6-well plates, changing pipette tips between plates, and rocked the plates to disperse the cell suspension evenly across the wells. We then transferred the seeded plates to a 37° C., 5% $CO_2$ incubator for 22+4 hours.

The work was carried out in a LFH until cells were fixed and thereafter in a fume hood. We would always leave a small amount of supernatant behind after centrifugations; this small step is especially important before fixation as the cells will aggregate easily if they are aspirated too dry. We then removed the plates out from the incubator, noting the date and time of removal. We then inspected the cells under a microscope and recorded degree of attachment and confluence. Using a sterile glass Pasteur pipette and a vacuum pump, we then aspirated media from all wells of a sample. We then added 0.5 ml of TrypLE™ express and left in on the cells as we moved on to the next sample. We changed the Pasteur glass between samples.

We then incubated the cells at room temperature ("RT") until the cells detached (this occasionally took more than 3 minutes). We then checked that the cells have detached under a microscope, as it is crucial that all cells have detached at this point. We then added 2 ml of pre-warmed growth media to each well in the same order that the TrypLE™ was added. We then pipetted carefully up and down to ensure all cells are in suspension. We then transferred the cells from each tube to a Falcon tube and centrifuge the tubes. We then aspirated medium from each tube, leaving about 50-100 gl of supernatant behind.

We then re-suspended the cells in remaining supernatant. We then added 1 ml of ice cold acetone: methanol to fix the cells and make them permeable, mixing by pipetting gently up and down. It is very important that cells are in single cell suspension at this point. We then incubated the samples at 4° C. for 15 to 60 minutes. We then added 1 ml of 1% BSA in PBS to each tube. We then centrifuged, then aspirated supernatant from each tube leaving about 50 100 μl of supernatant behind.

We then re-suspend the cells in remaining supernatant. We then added 70 μl of monoclonal antibody to each tube, and stained the cells with the antibody for 15 minutes at 4° C. For our experiments with adenovirus, we used antibody that is specific for adenoviral hexon capsid polypeptide. For another kind of virus, one may of course use an antibody specific for that kind of virus; the specific choice of virus and antibody are not important for the claimed invention.

We used a CANTO II™ brand fluorescence-activated cell sorter to count cells that contain fluorescent antibody-tagged polypeptide. The fluorescence-activated cell sorter was powered on before analysis and CST beads were first run as performance check. During running the first sample, we moved the P1 gate so that it covered the main population of cells. We prefer that data-collection settings should be such that each 96-well plate produces about 10,000 events in each P1 gate, and each tube produces about 50,000 events in each P1 gate.

Example 7

Non-Frozen Liquid Buffer Preserves Infectivity for At Least One Year. We prepared a suspension of virus in the buffer of Table 4, stored the suspension at −20 C for over one year, and periodically measured viral particle concentration. At −20° C., the buffer remained liquid (not frozen) due to the various salts and excipients included in it. Our experimental data show (Table 7) that total viral particle concentration over the course of a full year decreased, but insignificantly. Further, and more importantly, the infectious titer of the stored virus decreased a bit after three months, but then stabilized and thereafter remained quite high (as a percentage of the initial infectious titer) for at least one full year.

TABLE 7

Total Viral Particle and Infectious Viral Particle vs Time At −20° C. storage (Run Code #5)

| Time | Total viral particle concentration | % difference | Infectious titer | % difference |
|---|---|---|---|---|
| 0 | 3.1E+11 vp/ml [1] | 0% | 3.7E+10 | 0% |
| 3 | 3.0E+11 vp/ml [1] | −3% | 3.1E+10 | −16% |
| 6 | 2.8E+11 vp/ml [4] | −10% | 2.8E+10 | −24% |
| 9 | 2.9E+11 vp/ml [8] | −6% | 3.0E+10 | −19% |
| 12 | 3.0E+11 vp/ml [8] | −3% | 3.1E+10 [6] | −16% |

Notes:
Total viral particle concentration was measured using anion-exchange chromatography. Infectious titer was measured using fluorescence-activated cell sorting.
[1] Correction factor 0.862 was used. Correction factor was used as change of Working Standard (WS) concentration was not yet implemented. Results are comparable.
[4] Working Standard 2 concentration was changed and therefore correction of total viral particle concentration results using correction factor of 0.862 was no longer required. Results are comparable.
[6] Used nadofaragene firadenovec drug product as Reference Standard (RS).
[8] Deviation was raised to cover analysis of timepoint 9M and 12M total viral particle concentration (AEX-HPLC) using re-frozen samples. Timepoint 12M result is considered valid as 3 analyses done using original glass vial and 2 times re-frozen vial gave very similar results (RSD % 3%). Timepoint 9M and 12M results are considered valid as results are on the same level as seen for previous timepoint analyses (0M-6M) that were done using original vials stored at −20° C.

The remarkable stability achieved over one year with our temperature-responsive buffer system indicates that our buffer system will preserve infectivity in a liquid state for 18 months, 24 months, and longer storage.

Example 8

We repeated the protocol of Example 7. Those data again (Table 8) show stability of both viral particle concentration and infectious titer after 12 months of storage.

TABLE 8

Total Viral Particle and Infectious Viral Particle vs Time At −20° C. storage (Run Code #6)

| Time | Total viral particle concentration | % difference | Infectious titer | % difference |
|---|---|---|---|---|
| 0 | 3.2E+11 vp/ml [1] |  | 3.4E+10 |  |
| 3 | 3.0E+11 vp/ml [1] | −6% | 3.1E+10 | −9% |
| 6 | 3.1E+11 vp/ml [4] | −3% | 3.1E+10 | −9% |
| 9 | 2.8E+11 vp/ml [8] | −13% | 3.1E+10 | −9% |
| 12 | 3.1E+11 vp/ml | −3% | 2.7E+10 [6] | −21% |

For notes, see Example 7 above.

Example 9

We repeated the protocol of Example 7. Those data again (Table 9) show remarkable stability of viral particle concentration and infectious titer at 12 months storage.

TABLE 9

Total Viral Particle and Infectious Viral Particle vs Time At −20° C. storage (Run Code #7)

| Time | Total viral particle concentration | % difference | Infectious titer | % difference |
|---|---|---|---|---|
| 0 | 2.9E+11 vp/ml [1] |  | 3.6E+10 |  |
| 3 | 2.6E+11 vp/ml [1] | −10% | 3.0E+10 | −17% |
| 6 | 2.7E+11 vp/ml [6] | −7% | 2.9E+10 | −19% |
| 9 | 2.8E+11 vp/ml | −3% | 2.9E+10 | −19% |
| 12 | 2.9E+11 vp/ml | 0% | 3.1E+10 [6] | −14% |

For notes, see Example 7

Example 10

We repeated the protocol of Example 7. Those data (Table 10) again show stability of both viral particle concentration and infectious titer after 12 months of storage.

TABLE 10

Total Viral Particle and Infectious Viral Particle vs Time At −20° C. storage (Run Code #8)

| Time | Total viral particle concentration | % difference | Infectious titer | % difference |
|---|---|---|---|---|
| 0 | 3.1E+11 vp/ml [1] |  | 3.7E+10 |  |
| 3 | 3.0E+11 vp/ml [1] | −3% | 3.1E+10 | −16% |
| 6 | 2.8E+11 vp/ml [4] | −10% | 2.8E+10 | −24% |

TABLE 10-continued

Total Viral Particle and Infectious Viral Particle vs Time
At −20° C. storage (Run Code #8)

| Time | Total viral particle concentration | % difference | Infectious titer | % difference |
|---|---|---|---|---|
| 9 | 2.9E+11 vp/ml [8)] | −6% | 3.0E+10 | −19% |
| 12 | 3.0E+11 vp/ml [8)] | −3% | 3.1E+10 [6)] | −16% |

For notes, see Example 7

Example 11

One repeats the protocol of Example 7, using the preparation of Example 1. Those data again (Table 11) show stability of both viral particle concentration and infectious titer after 12 months of storage.

TABLE 11

Total Viral Particle and Infectious Viral Particle vs Time
At −20° C. storage

| Time | Total viral particle concentration | % difference | Infectious titer | % difference |
|---|---|---|---|---|
| 0 | | | | |
| 3 | | −5% | | −17% |
| 6 | | −5% | | −17% |

TABLE 11-continued

Total Viral Particle and Infectious Viral Particle vs Time
At −20° C. storage

| Time | Total viral particle concentration | % difference | Infectious titer | % difference |
|---|---|---|---|---|
| 9 | | −5% | | −17% |
| 12 | | −5% | | −17% |

For notes, see Example 7

Example 12: Extension of Storage Time at Refrigerated Conditions

A study was conducted using a suspension of virus (e.g., nadofaragene firadenovec) in the buffer of Table 5 to examine two different storage conditions: (a) storage for 7 days at a refrigerator temperature (2-8° C.); and (b) storage for 7 days at a refrigerator temperature (2-8° C.) followed by 24 hours at room temperature (20-25° C.). The appearance, particle size distribution, pH, total viral particle concentration, infectious titre, potency and NODA concentration were analyzed using validated analytical methods. The results of the handling stability study after 7 days at refrigerator temperature with or without 24 hours storage at room temperature are shown in the below Tables 12A and 12B. As shown in the tables, all samples met the acceptance criteria according to the specification for all parameters tested and no effects of the viral handling were observed compared to t=0 results.

TABLE 12A

| Test | Acceptance Criteria | t = 0[1] | 7 days at 2-8° C. | 7 days at 2-8° C. + 24 hours at RT |
|---|---|---|---|---|
| Appearance | Opalescent colorless solution, practically free of visible particles | Conforms | Conforms | Conforms |
| Particle size distribution | 86-151 nm | 123 nm | 123 nm | 123 nm |
| pH | 7.6-8.0 | 7.8 | 7.8 | 7.8 |
| Viral particle concentration | $2.4$-$3.7 \times 10^{11}$ Vp/mL | $3.1 \times 10^{11}$ vp/mL | $3.1 \times 10^{11}$ vp/mL | $3.2 \times 10^{11}$ vp/mL |
| Infectious titre | $2.4$-$4.9 \times 10^{10}$ NAS IU/mL | $3.0 \times 10^{10}$ NAS IU/mL | $3.8 \times 10^{10}$ NAS IU/mL | $4.1 \times 10^{10}$ NAS IU/mL |
| Potency | 0.67-1.84 U/vp | 1.68 U/vp | 1.28 U/vp | 1.32 U.vp |
| Syn3NODA concentration | 0.76-1.19 mg/mL | 0.88 mg/mL | 0.93 mg/mL | 0.91 mg/mL |

[1]data from latest completed time point in ongoing long-term stability study

TABLE 12B

| Test | Acceptance Criteria | t = 0[1] | 7 days at 2-8° C. | 7 days at 2-8° C. + 24 hours at RT |
|---|---|---|---|---|
| Appearance | Opalescent colorless solution, practically free of visible particles | Conforms | Conforms | Conforms |
| Particle size distribution | 86-151 nm | 109 nm | 110 nm | 111 nm |
| pH | 7.6-8.0 | 7.8 | 7.8 | 7.8 |
| Viral particle concentration | $2.4$-$3.7 \times 10^{11}$ Vp/mL | $2.8 \times 10^{11}$ vp/mL | $2.9 \times 10^{11}$ vp/mL | $2.8 \times 10^{11}$ vp/mL |
| Infectious titre | $2.4$-$4.9 \times 10^{10}$ NAS IU/mL | $2.6 \times 10^{10}$ NAS IU/mL | $3.6 \times 10^{10}$ NAS IU/mL | $3.6 \times 10^{10}$ NAS IU/mL |
| Potency | 0.67-1.84 U/vp | 1.10 U/vp | 1.24 U/vp | 1.31 U/vp |
| Syn3NODA concentration | 0.76-1.19 mg/mL | 0.86 mg/mL | 0.87 mg/mL | 0.87 mg/mL |

[1]Release data/t = 0 in long term stability study

Example 13: Extension of Nadofaragene Firadenovec Syringe Time to 6 Hours

A study was conducted using frozen samples of nadofaragene firadenovec suspended in the buffer of Table 5. The samples used thawed and equilibrated in 30R vials at room temperature for 16 hours. Thereafter, the dose was withdrawn into polypropylene syringes through a vial adapter and kept in the syringe for 6 hours. References stored in the 30R vials under the same conditions as the test samples were included for comparison. After 6 hours at room temperature (protected from light), appearance, pH, viral particle concentration, infectious titre, potency, particle size distribution, and NODA concentration (all performed in triplicates) were analyzed using validated analytical methods.

TABLE 13

| Test | Acceptance Criteria | | |
|---|---|---|---|
| Appearance | Opalescent colorless solution, practically free of visible particles | Conforms Conforms Conforms | Conforms Conforms Conforms |
| Particle size distribution | 86-151 nm | 112 111 111 | 113 112 112 |
| pH | 7.6-8.0 | 7.8 7.8 7.7 | 7.8 7.8 7.8 |
| Viral particle concentration | 2.4-3.7 × $10^{11}$ Vp/mL | 3.1 × $10^{11}$ 3.2 × $10^{11}$ 3.1 × $10^{11}$ | 3.2 × $10^{11}$ 3.1 × $10^{11}$ 3.1 × $10^{11}$ |
| Infectious titre | 2.4-4.9 × $10^{10}$ NAS IU/mL | 3.3 × $10^{10}$ 2.6 × $10^{10}$ 3.8 × $10^{10}$ | 3.3 × $10^{10}$ 2.9 × $10^{10}$ 3.4 × $10^{10}$ |
| Potency | 0.67-1.84 U/vp | 1.20 1.21 1.26 | 1.26 1.19 1.26 |
| Syn3NODA concentration | 0.76-1.19 mg/mL | 0.97 0.96 0.95 | 0.96 0.97 0.96 |

Example 14: 48-Month Stability Study of Nadofaragene Firadenovec

A stability study was conducted using a suspension of virus (e.g., nadofaragene firadenovec) in the buffer of Table 5 frozen for 48 months at below −60° C. The data is shown below in Table 14. The data shows no loss of activity of the virus during the entirety of the 48 months of storage.

TABLE 14

| Test | Acceptance criteria | Relative acceptance criteria | Storage conditions (° C.) | Storage time (months) | |
|---|---|---|---|---|---|
| | | | | 0 | 3 |
| Appearance | Opalescent colourless solution, practically free of visible particles | Comparable to T = 0 | Below −60 | Conforms | Conforms |
| Particle size distribution (nm) | 86-151 | None set | Below −60 | 117[a] | 117 |
| pH | 7.6-8.0 | None set | Below −60 | 7.8 | 7.8 |
| Viral particle concentration (× $10^{11}$ vp/mL) | 2.4-3.7 | ±20% of T = 0 result | Below −60 | 3.0 | 3.0 |
| Infectious titre (× $10^{10}$ NAS IU/mL) | 2.1-4.9 | ±50% of T = 0 result | Below −60 | 4.3[a, b] | 4.3 |
| Potency (U/vp) | 0.67-1.84 | ±50% of T = 0 result | Below −60 | 1.13[a] | 1.13 |
| Sterility | Sterile | Sterile | Below −60 | Sterile[d] | — |
| NODA concentration (mg/mL)[c] | 0.76-1.19 | None set | Below −60 | — | — |

| | Storage time (months) | | | | | | |
|---|---|---|---|---|---|---|---|
| Test | 6 | 9 | 12 | 18 | 24 | 36 | 48 |
| Appearance | Conforms | Conforms | Conforms | Conforms | Conforms | Conforms | Conforms |
| Particle size distribution (nm) | 116 | 116 | 119 | 118 | 118 | 118 | 118 |
| pH | 7.8 | 7.8 | 7.8 | 7.8 | 7.8 | 7.8 | 7.8 |
| Viral particle concentration (× $10^{11}$ vp/mL) | 2.9 | 3.0 | 3.3 | 3.2 | 3.0 | 3.1 | 3.0 |
| Infectious titre (× $10^{10}$ NAS IU/mL) | 4.6 | 3.4 | 4.1 | 4.4 | 5.0[f] | 4.5 | 4.7 |
| Potency (U/vp) | 1.06 | 1.11 | 1.29 | 1.31 | 1.24 | 1.38 | 1.31 |
| Sterility | — | — | — | — | — | — | Sterile |
| NODA concentration (mg/mL)[c] | — | 0.98[e, g] | — | 0.89[g] | 0.87[g] | 0.96[h] | 0.92[h] |

[a]Timepoint 0M particle size, infectious titre and potency assays were performed using a total viral particle concentration (vp/mL, by HPLC) result that was later corrected according to an internal change control. The stability study is continued with the same uncorrected viral particle titer until the end of the stability study to enable accurate comparison between timepoints. As the difference between the correct and incorrect titer is minor (under 15%) and the result of these three assays are well within the specification, there is no impact to the stability study.

[b]Timepoint 0M infectious titre result is average of 2 Test Samples results (4.6 × 1010 NAS IU/mL and 4.0 × $10^{10}$ NAS IU/mL).

[c]The NODA concentration test was added to the study after the start of the stability testing of the batch. The test was included at timepoint 18M.

[d]Sterility testing was performed according to Ph.Eur.2.6.1, membrane filtration method.

[e]NODA concentration was measured as part of the comparability study at timepoint 9M.

[f]Infectious titre result is above acceptance criterion. OOS investigation performed. Results do not show any loss of activity and can be considered valid

[g]Analysis performed with tentative analytical procedure available at time of analysis, not fully validated.

[h]Analysis performed with final, validated analytical procedure.

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of preserving the infectivity of an infective virus, the method comprising the steps of:
storing a composition comprising an infective virus in a frozen state at a temperature lower than or equal to −60° C. for at least one year to preserve the infectivity of the virus,
wherein the virus is an infective replication-deficient adenovirus encoding interferon α-2b;
further wherein the composition comprises the virus and a final buffer which is made from a combination of one part (w/w) of a buffer formulation with nine parts (w/w) purified water;
further wherein, the virus is suspended in the composition at a concentration of about $3 \times 10^{11}$ adenoviral particles per mL of buffer; and
still further wherein, the buffer formulation comprises the following components, in an amount (w/w) of each component expressed as a percent of the weight of tromethamine used to make the buffer:
about 6000% glycerol;
about 1214% sucrose;
about 100% tromethamine;
about 100% sodium dihydrogen phosphate dihydrate;
about 560% hydroxypropyl beta-cyclodextrin;
about 29% magnesium chloride hexahydrate;
about 68% (3α,53,7α,12α)-N-[3-[(4-O-D-galactopyranosyl-D-gluconoyl)aminolpropyl]-3,7,12-trihydroxy-N [3-[[(3α,53,7α,12α)-3,7,12-trihydroxy-24-oxocholan-24-yl]amino]propyl]-cholan-24-amide (NODA)
about 34% polysorbate 80;
about 2.8% sodium citrate dihydrate; and
about 0.71% citric acid monohydrate.

2. The method of claim 1, wherein after storage in a frozen state at a temperature lower than or equal to −60° C. for at least one year, the particles retain at least about 95% of the initial total particle concentration and at least about 80% of their initial infectious titer as measured as Normalized and Adjusted Standard-Infectious Units (NAS IU).

3. The method of claim 1, wherein the temperature is about −60° C. to about −100° C., about −60° C. to about −90° C. or about −60° C. to about −80° C.

4. The method of claim 1, wherein the composition is stored in a frozen state for at least 18 months, at least 24 months, or at least 36 months.

5. The method of claim 1, wherein the buffer formulation has a basic pH at temperatures of about −60° C. and an acidic pH at temperatures of about 20° C. to about 25° C.

* * * * *